United States Patent
Usowicz et al.

(10) Patent No.: US 9,075,035 B2
(45) Date of Patent: Jul. 7, 2015

(54) INJECTION PORT NEEDLE SUPPORT AND WASHING

(75) Inventors: James E. Usowicz, Webster, MA (US); Tony A. Lin, Ashland, MA (US); Joshua A. Burnett, Taunton, MA (US); Marc Lemelin, Douglas, MA (US)

(73) Assignee: Waters Technologies Corporation, Milford, MA (US)

( * ) Notice: Subject to any disclaimer, the term of this patent is extended or adjusted under 35 U.S.C. 154(b) by 245 days.

(21) Appl. No.: 13/520,610

(22) PCT Filed: Jan. 10, 2011

(86) PCT No.: PCT/US2011/020630
§ 371 (c)(1),
(2), (4) Date: Oct. 1, 2012

(87) PCT Pub. No.: WO2011/085285
PCT Pub. Date: Jul. 14, 2011

(65) Prior Publication Data
US 2013/0019699 A1    Jan. 24, 2013

Related U.S. Application Data

(60) Provisional application No. 61/293,902, filed on Jan. 11, 2010.

(51) Int. Cl.
*G01N 1/02* (2006.01)
*G01N 30/18* (2006.01)
*G01N 35/10* (2006.01)

(52) U.S. Cl.
CPC ............ *G01N 30/18* (2013.01); *G01N 35/1004* (2013.01); *G01N 35/1009* (2013.01); *G01N 35/1097* (2013.01); *G01N 2030/185* (2013.01)

(58) Field of Classification Search
CPC ... G01N 30/24; G01N 30/18; G01N 35/1095; G01N 30/20
USPC ........................................................ 73/864.85
See application file for complete search history.

(56) References Cited

U.S. PATENT DOCUMENTS 4,094,196 A    6/1978  Friswell
4,094,197 A    6/1978  Harris, Sr. et al.
(Continued)

FOREIGN PATENT DOCUMENTS

DE        2026329        12/1971
EP     0 141 148 A1       5/1985
(Continued)

OTHER PUBLICATIONS

Snyder, L. R., et al., "Introduction to Modern Liquid Chromatography", Second Edition, John Wiley & Sons, Inc. (1979), Chapter 3, 43 pp.
(Continued)

*Primary Examiner* — Hezron E Williams
*Assistant Examiner* — Rodney T Frank
(74) *Attorney, Agent, or Firm* — Muirhead and Saturnelli, LLC

(57) ABSTRACT

Described are techniques for use with an injection port. The injection port includes a needle support structure configured to accommodate a needle containing a sample aspirated therein. The injection port includes a needle seal having a first surface thereof in contact with a second surface of a tip of the needle. A seal is formed when the first surface contacts the second surface and a sufficient force is applied to the needle.

18 Claims, 10 Drawing Sheets

(56) References Cited

U.S. PATENT DOCUMENTS

| | | |
|---|---|---|
| 4,624,148 A | 11/1986 | Averette |
| 5,012,845 A | 5/1991 | Averette |
| 5,032,151 A | 7/1991 | Klein et al. |
| 5,114,161 A | 5/1992 | Sgourakes et al. |
| 5,756,905 A | 5/1998 | Ueda |
| 6,526,812 B2 | 3/2003 | Martin et al. |
| 7,219,566 B1 | 5/2007 | Maeda |
| 2007/0095158 A1 | 5/2007 | Maeda |

FOREIGN PATENT DOCUMENTS

| | | |
|---|---|---|
| EP | 1 275 957 A2 | 1/2003 |
| EP | 1 808 700 A2 | 7/2007 |
| WO | WO 2007/067540 A1 | 6/2007 |

OTHER PUBLICATIONS

European Supplementary Search Report dated Sep. 25, 2014.

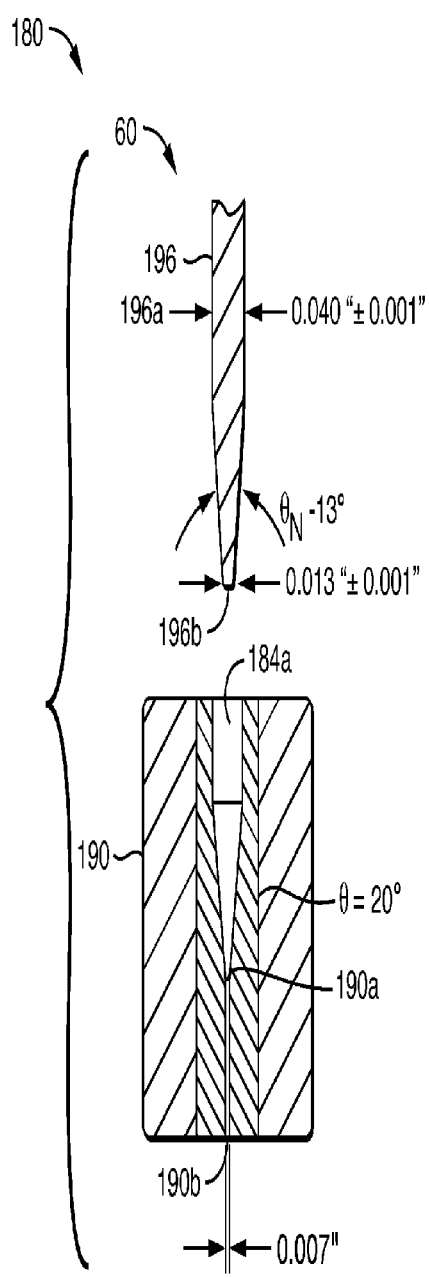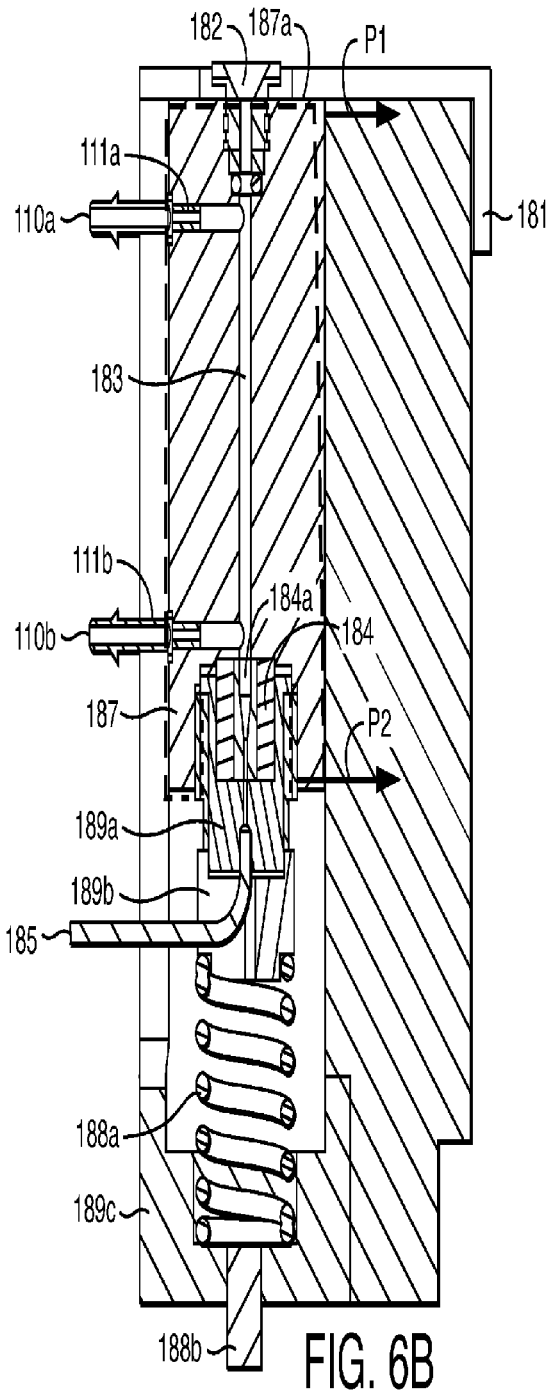
FIG. 6A
FIG. 6B

INJECTION PORT NEEDLE SUPPORT AND WASHING

CROSS REFERENCE TO RELATED APPLICATIONS

This application is a National Stage of International Application No. PCT/US2011/20630, filed Jan. 10, 2011, which claims priority to U.S. Provisional Application No. 61/293,902, filed Jan. 11, 2010, which are hereby incorporated by reference.

BACKGROUND

1. Technical Field

This application generally relates to sample introduction, and more particularly to techniques used in connection with sample injection apparatus and techniques.

2. Description of Related Art

Samples may be processed in a laboratory or other environment for a variety of different purposes and applications. Chromatography refers to techniques for separating sample mixtures. Common chromatographic techniques include gas chromatography (GC) and liquid chromatography (LC). With an instrument that performs LC, a liquid sample to be analyzed is introduced in small volumes for analysis. The sample may be injected into a solvent stream which is carried through a column. The compounds in the sample can then be separated by traveling at different speeds through the column resulting in the different compounds eluting from the column at different times. In connection with High Performance Liquid Chromatography (HPLC) and Ultra Performance Liquid Chromatography (UPLC), pressure is used to facilitate fluid flow in the system through the chromatographic column.

In a system that performs LC, a sample may be injected into the system using different techniques. One technique is fixed loop injection where a sample may be aspirated into a needle, positioned in a sample loop, and then carried through to the column. With fixed loop injection, the sample loop becomes part of the fluid path. Another technique is direct injection where a sample is aspirated into a needle and the sample is directly injected into the system so that the needle becomes part of the fluid path. With direct injection, after the sample is aspirated into a needle, the needle may be positioned at a surface of a sealing member. The needle has sufficient force applied thereto so that the needle tip forms a seal at the surface of the sealing member when the LC system is subsequently pressurized. The sample in the needle is then carried through to the column, such as by a solvent. The needle used with direct injection may be subject to buckling due to the amount of force applied in connection with forming the seal. Additionally, needle washing is part of the processing typically performed in connection with direct injection techniques. After the sample is injected and after completion of the associated chromatographic run for the sample, the needle may be subject to a wash sequence where the outside of the needle is washed with a solvent, solution, or the like, to remove any remaining sample from the needle.

SUMMARY OF THE INVENTION

In accordance with one aspect of the invention is an injection port including a needle support structure and a needle seal. The needle support structure is configured to accommodate a needle containing a sample aspirated therein. The needle seal has a first surface thereof in contact with a second surface of a tip of the needle, wherein a seal is formed when the first surface contacts the second surface and a sufficient force is applied to the needle. The needle support structure may be formed from a material having a passageway into which the needle is inserted when forming the seal. The injection port may be included in a system that performs liquid chromatography. The material is one of a PEEK (polyether-ether-ketone) material or stainless steel. The needle support structure may include a first port connected to the passageway and a second port connected to the passageway. Washing fluid may enter the passageway through the first port and exit the passageway through the second port. The first port may be connected to a solvent source used as the washing fluid and the second port is connected to waste. The first port may be connected to the passageway through a first connection and the second port may be connected to the passageway through a second connection. The first connection and the second connection may be included in the needle support structure and may be approximately perpendicular with respect to the passageway. Washing fluid may enter the passageway through the first port connected approximately perpendicular to the passageway and may exit through the second port connected to an opening at a top of the passageway into a wash overflow component which diverts to waste. The needle may be inserted at a first end of the passageway and the tip of the needle forms the seal when in contact with a surface of the needle seal at an opposing end of the passageway. Washing fluid may pass through the passageway to wash the needle while a seal is formed between surfaces of the needle seal in contact with surfaces of a tip of the needle.

In accordance with another aspect of the invention is a method of performing direct injection of a sample comprising: receiving a needle having the sample aspirated therein; inserting the needle into a passageway of a needle support structure; applying a sufficient force to the needle to form a seal between surfaces of a tip of the needle in contact with surfaces of a needle seal; and transporting the sample from the needle over a fluid path to a liquid chromatography column for separation. The needle support structure may provide support for the needle to prevent buckling when pressure is applied thereto to form the seal. The method may also include washing the needle with washing fluid that flows through the passageway while the seal is formed. The washing may be performed prior to completion of a chromatographic run of the sample. The needle may be inserted at a first end of the passageway and the tip of the needle forms the seal when in contact with a surface of the needle seal at an opposing end of the passageway.

BRIEF DESCRIPTION OF THE DRAWINGS

Features and advantages of the present invention will become more apparent from the following detailed description of exemplary embodiments thereof taken in conjunction with the accompanying drawings in which:

FIGS. 6 and 7 are examples example illustrating components that may be included in an embodiment in accordance with techniques described herein.

DETAILED DESCRIPTION OF EMBODIMENT(S)

Figure 1A:
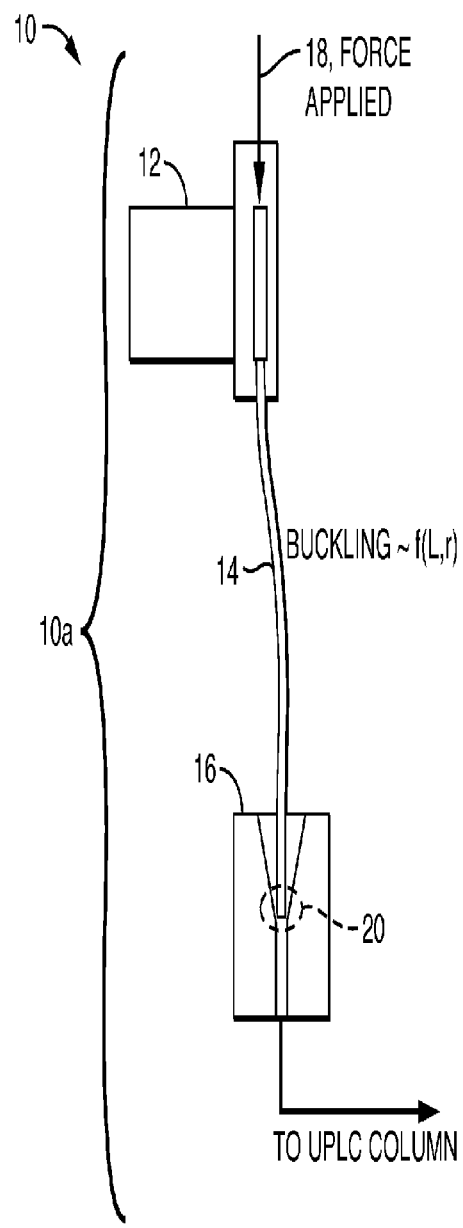
FIG. 1 is an example illustrating problems that may occur with an embodiment of an injection port without use of the needle support structure described herein.

Described in following paragraphs are techniques that may be used in connection with providing a needle support structure and performing needle washing. Techniques described in following paragraphs may be used in connection with an embodiment such as a liquid chromatography (LC) system. The LC system may be, for example, a High Performance Liquid Chromatography (HPLC) or an Ultra Performance Liquid Chromatography (UPLC) system such as the ACQUITY UPLC® and nanoACQUITY UPLC® systems from Waters Corporation of Milford Mass. An LC system such as the foregoing from Waters Corporation may operate under high pressure such as in the range of 5,000 pounds per square inch or psi (e.g, exemplary for some HPLC systems) to 15,000-20,000 psi (exemplary for some UPLC systems). The foregoing exemplary pressures should not be construed as a limitation. The techniques herein may be used in an embodiment of an LC or other system which operates at pressures different from, and/or higher than, the foregoing exemplary pressures. An LC system may include an injector used to inject controlled volumes of a sample, either manually or automatically, into a fluid stream which carries the sample to an LC column where the sample may then be separated. As described in following paragraphs and figures, an exemplary embodiment in accordance with techniques described herein may be a UPLC or HPLC system using direct injection to introduce a sample for analysis. In a direct injection LC system, a sample may be aspirated into a needle and the needle becomes part of the system flow path. For example, the Alliance HPLC® System by Waters Corporation uses direct injection.

As known in the art, an LC system using direct injection may aspirate a sample into a needle and position the needle at a surface of a sealing member. The needle may have a sufficient force applied thereto so that the needle tip forms a seal at the surface of the sealing member when the LC system is subsequently pressurized. The sample in the needle is then transported from the needle over a fluid path and carried through to the column, such as by a solvent. The techniques described in following paragraphs may be used to provide a support structure for the needle and also to perform washing of the needle. As explained in more detail below, the support structure may alleviate buckling of the needle when a force is applied thereto to form a seal. Additionally, needle washing prevents sample carryover between injections and may extend the life of the injector needle seal.

In connection with direct injection, the needle may be inserted into sample vials, plates, wells, and the like, (or more generally sample containers) from which a sample is drawn. The containers may have a variety of different dimensions (e.g., diameter and depth or length). As such, the needle in an LC system may accommodate use with any of the variety of different container dimensions. For example, the needle may have a diameter selected in accordance with a smallest or minimum expected container diameter and may have a length selected in accordance with a largest or maximum expected container length. As a further example, the needle used in an embodiment of a LC system with direct injection in accordance with techniques herein may have a diameter in the inclusive range of 0.040 to 0.062 inches and a length of approximately 2.5 inches.

A needle having dimensions similar to that as described above may buckle easily when a required force is applied to the needle to form the seal. As such, it may be desirable to provide a support structure for the needle used in connection with direct injection. An embodiment of an injection port as described herein may include such a support structure. Use of the support structure effectively increases stiffness of the needle to avoid buckling due to the force applied to the needle in connection with forming the seal. Additionally, the port design may optionally include features used in connection with washing the exterior surfaces of the needle while the seal is formed prior to completion of the injection and chromatographic run. As will be illustrated in a following figure, the support structure may provide an additional advantage of reducing needle misalignment at the point where the seal is formed at contact surfaces of the needle seal and needle tip.

Figure 1B:
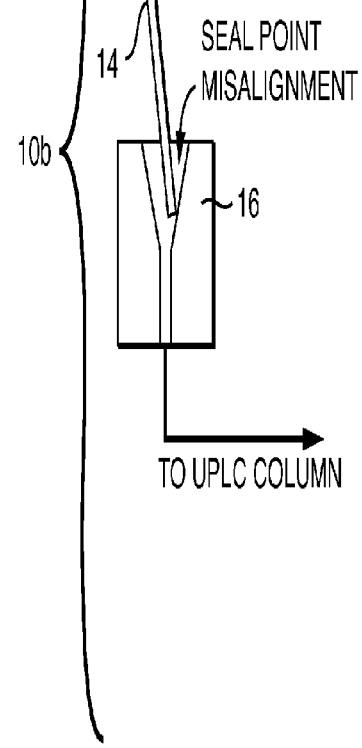

Referring to FIG. 1, shown are examples illustrating problems that may occur in connection with direct injection without use of the techniques described herein. It should be noted that the examples of 10 include only selected parts of an injection port that may be used in connection with direct injection for purposes of illustration.

FIG. 1 includes a first example 10*a* illustrating needle buckling that may occur in connection with direct injection without the benefit of the additional needle support in accordance with techniques herein. The example 10*a* includes a positioning arm 12, needle 14 and needle seal 16. The arm 12 may facilitate movement and positioning of the needle 14 and may serve as the holder of the needle 14. Although not illustrated, the arm 12 may be controlled in an automated fashion using a motor to facilitate movement of the arm over a sample container from which a sample is drawn upward into the needle. Subsequent to the foregoing sample aspiration into the needle, the arm 12 may be moved and positioned as illustrated in 10*a* to inject the sample in the needle into the system. In preparation for sample injection, the parts are positioned as in the example 10*a* and a sufficient force 18 is applied to the needle 14 to form a seal within 20 where the surfaces of the tip of the needle 14 contact the surfaces of the needle seal 16. As known in the art, the amount of force that can be applied to the needle without causing the needle to buckle may be generally characterized as a function of the length and the radius of the needle. In other words, the amount of buckling, if any, which occurs may be characterized as a function (f) of the needle's radius (r) and length (L) (e.g., f(L,r)).

The example 10*b* illustrates misalignment that may occur at the sealing point with respect to the needle seal and needle (e.g., at points of contact between surfaces of the needle tip and sealing member). The arm 12 may not be horizontally positioned in exact proper alignment with the needle seal resulting in the illustrated misalignment of 10*b*.

Figure 2:
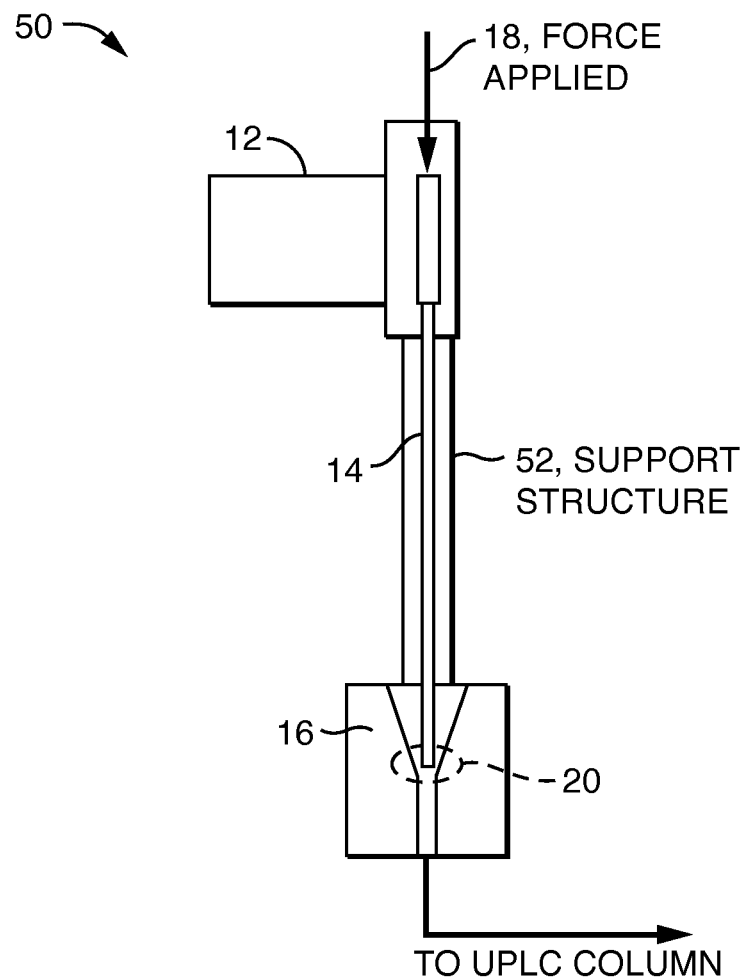
FIG. 2 is an example illustrating use of a needle support structure in an embodiment in accordance with techniques herein.

Referring to FIG. 2, shown is an example of an embodiment of a needle support structure in accordance with techniques herein. The example 50 includes similarly numbered parts from FIG. 1. The example 50 also includes a support structure 52 providing additional needle support (relative to the examples of FIG. 1). As such, an embodiment of an injection port in accordance with techniques herein may include the features of the support structure 52. Additional details regarding the support structure and injection port are provided in connection with other figures and description herein. In one embodiment, element 52 may correspond to a tube or cylindrical shaped structure, such as made of stainless steel or a PEEK (polyether-ether-ketone) material, having sufficient dimensions to accommodate the needle 14. In another embodiment as described in following paragraphs, element 52 may be a passageway formed in surrounding material so that the support structure may include the passageway into which the needle is inserted and also the surrounding material.

By having the needle support structure which encases or surrounds the needle, an embodiment of the injection port may also include features for needle washing. In such an embodiment in accordance with techniques herein, the needle washing may be performed while the seal is formed (e.g., while needle tip and needle seal are engaged in forming the substantially fluid tight seal). As such, an embodiment in accordance with techniques herein may perform needle washing once the foregoing fluid tight seal is formed such as in connection with sample injection. This is described in more detail in following paragraphs.

It should be noted that the needle support structure of FIG. 2 is one part that may be incorporated into an injection port. A more detailed example of an injection port that may be included in an embodiment, such as in an LC system, is included in other figures herein. FIG. 2 illustrates an example of a needle support structure that may be included in an embodiment in which the needle support is provided without additional features for needle washing in accordance with techniques herein. Other examples of needle support structures that may be used in connection with providing the needle support in combination with the needle washing techniques and features described herein are provided in other figures.

Figure 3:
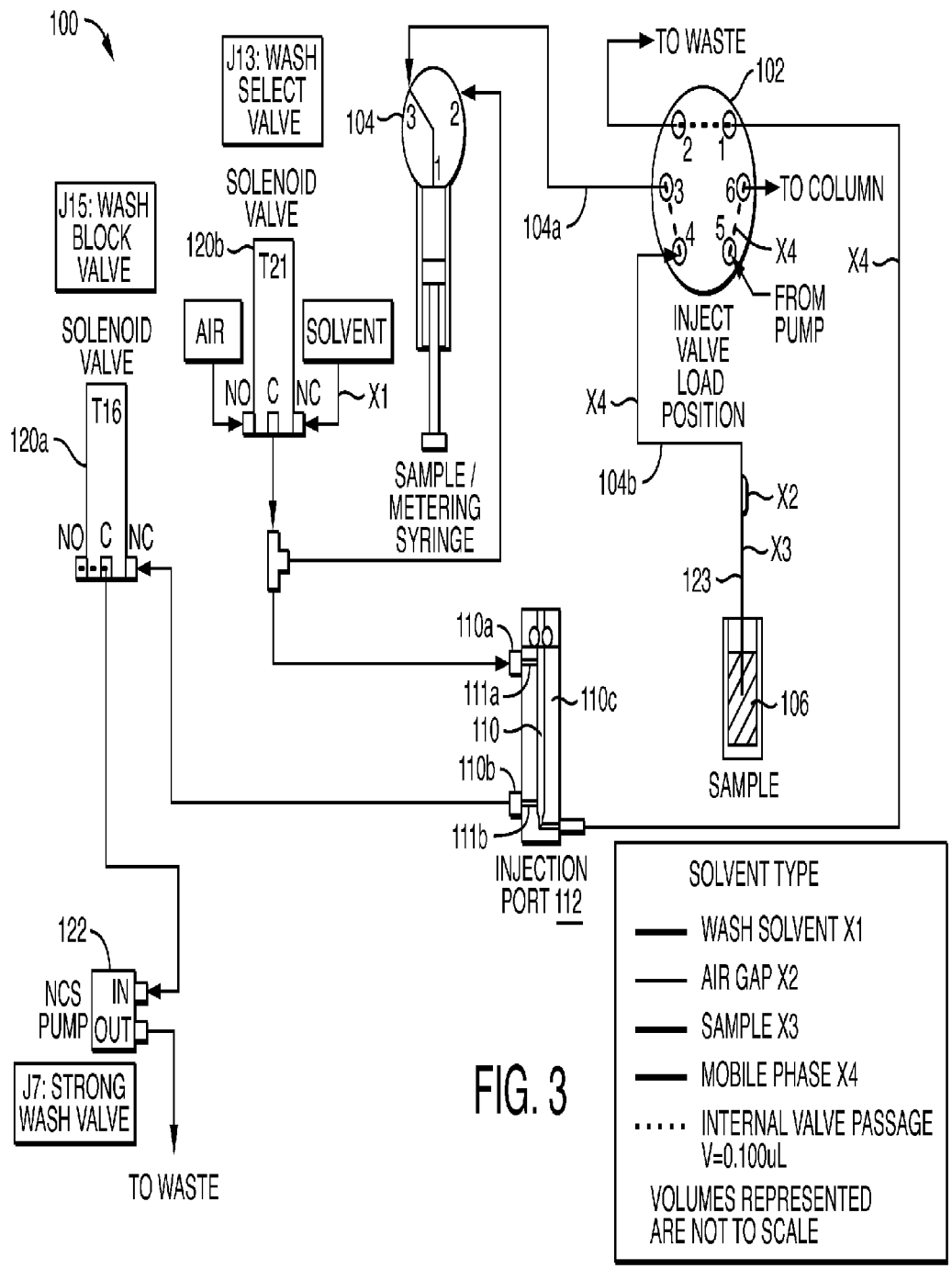
FIGS. 3 and 4 are examples illustrating use of components in an embodiment in accordance with techniques herein.

Referring to FIG. 3, shown is an example of a system including an embodiment of an injection port in accordance with techniques herein. The example 100 illustrates components that may be included in an embodiment of an LC system. The example 100 includes an injection valve 102, pump 122, injection port 112, other valves 120a, 120b, syringe 104, and sample 106. Components of the example 100 may be interconnected by one or more types of suitable conduits or tubings used in forming the fluidic paths of the LC system. The example 100 may illustrate the state of the components and connections therebetween when a sample is being aspirated into the needle 123. The portion(s) X1 denote the paths containing wash solvent. In this example, the path is connected to a solvent source. The portion X2 denotes an air gap. The portion X3 denotes the presence of the sample in the needle. The portions X4 denote presence of the mobile phase in the indicated paths and connections.

When the sample is being aspirated into the needle as illustrated in 100, the injection valve 102 is in the load position. The syringe 104 may be used to aspirate a sample volume into the needle 123 when the needle 123 is inserted into the container 106 containing the sample. The syringe 104 facilitates drawing the sample into the needle since the injection valve in the load position connect ports 3 and 4 defining a path from the syringe 104 through 104a, ports 3 and 4, 104b and to the needle 123. As known in the art, the injection valve 102 may be rotated to different positions to provide different fluidic connections between ports (e.g., denoted 1-6) of the valve. Rotation of the valve 102 causes channels or grooves of valve components, such as grooves that may be formed in the surface of a valve rotor, to connect different ports of the valve 102. Those ports which are connected to form fluidic paths when the valve 102 is in the load position are illustrated by the dashed lines between ports in the example 100.

It should be noted that valves, such as injection valve assemblies represented by element 102, are known in the art and described, for example, in U.S. Provisional Patent Application No. 61/293,879, filed Jan. 11, 2010, STATIC AND DYNAMIC SEALS, ("STATIC AND DYNAMIC SEALS application"), which is incorporated by reference herein, and WO 2005/079543 A2 (PCT/US2005/005714) PIN VALVE ASSEMBLY, Keene et al., which is incorporated by reference herein. A valve, such as an injector valve 102 that may be used in an LC system, may include a stator and a rotor acting together to connect or align ports of the valve. The rotor may be actuated in a rotational manner relative to the axis of the valve in order to vary the position of the rotor relative to the stator, which remains stationary. A first surface of the rotor may face a surface of the stator. The rotor may be a removable disk which may include a pattern of the grooves formed on the first surface. The rotor may be included in a valve assembly including a drive shaft coupled to another component, such as an engine or motor, to facilitate actuating the valve assembly such as in connection with loading a volume of sample.

The injection port 112 includes a support structure for the needle formed by a passageway 110 and surrounding material 110c. Additionally, the injection port 112 and its support structure may also include ports 110a and 110b with respective connections 111a and 111b to the passageway 110 for use in needle washing in accordance with techniques herein. The foregoing features and use in needle washing are described in more detail in following paragraphs.

Figure 4:
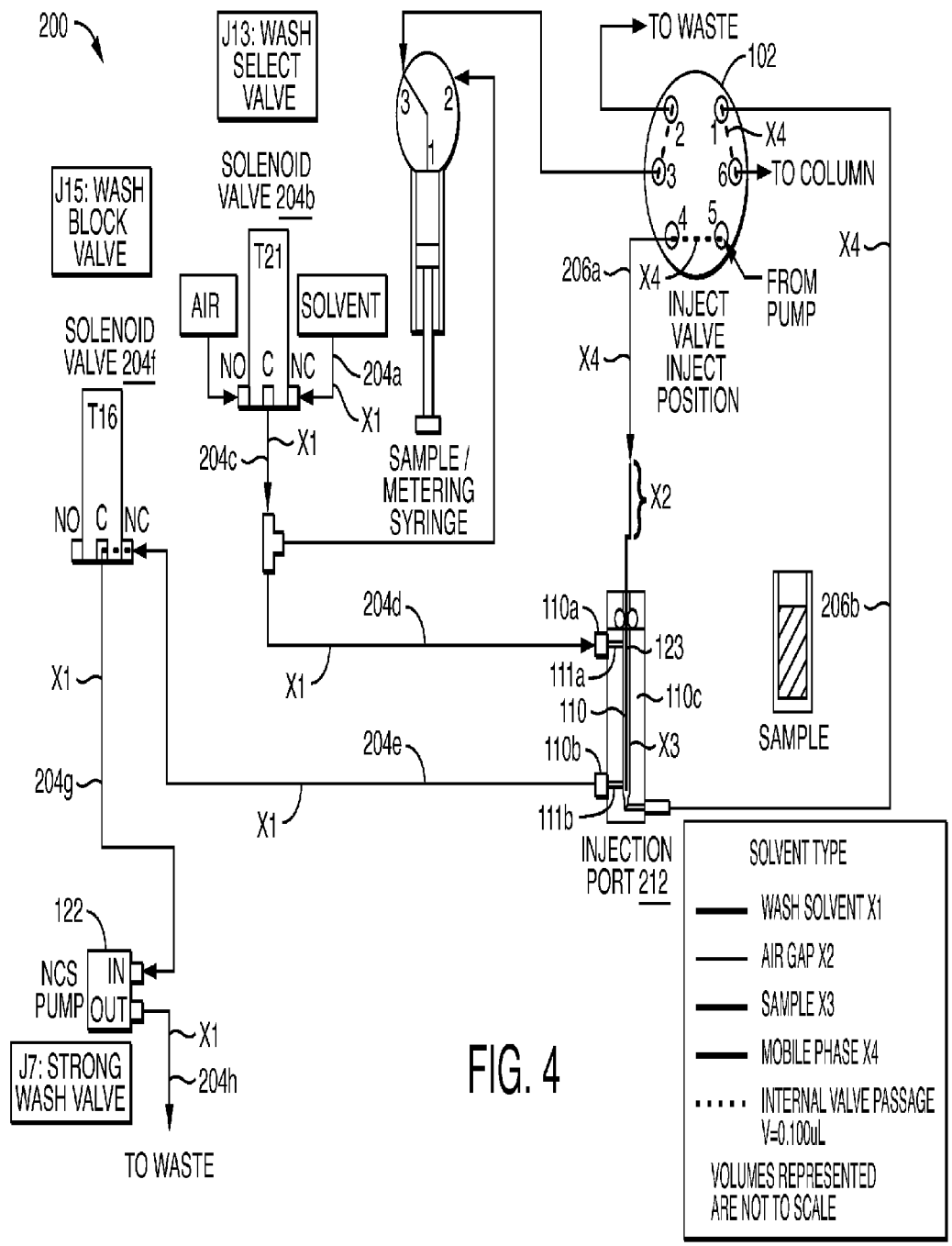

Once the sample has been aspirated into the needle, processing is performed to inject the sample into the system as illustrated by FIG. 4. As will be described below, the processing may include rotating the injection valve from a load to an inject position, inserting the needle into the injection port with sufficient force to form a seal between surfaces of the needle tip and needle seal, and forcing the sample from the needle to the LC column over a fluid path. Additionally, in accordance with techniques herein, an embodiment may perform needle washing once the foregoing seal is formed while the sample is being injected into the system and analyzed as part of the chromatographic run.

Referring to FIG. 4, shown is an example including the components of FIG. 3 illustrating injection of the sample into the system. In the example 200, the injection valve 102 is in the inject position. To facilitate injection of the aspirated sample in the needle 123, the valve 102 may be rotated from a first load position of FIG. 3 to the second inject position of FIG. 4 providing fluidic connections between valve ports. Those ports of the valve 102 which are connected to form the fluidic paths when in the inject position are illustrated by the dashed lines between ports in the example 200. The needle 123 (with aspirated volume of a sample therein) may be inserted as illustrated in the example 200 into the injection port with a sufficient force applied thereto to form a seal between a needle seal and the tip of the needle. It should be noted that the needle seal is not visible in detail in connection with FIGS. 3 and 4 but is illustrated in more detail in connection with other figures. Examples and additional detail regarding a needle, needle seal, force sensor, forces applied to the needle, and other aspects related to the injection port as may be used in an embodiment in connection with techniques herein with direct injection are described for example, in U.S. Provisional Patent Application No. 61/293,889, filed Jan. 11, 2010, NEEDLE SEAL FORCE SENSOR ("NEEDLE SEAL FORCE SENSOR patent application"), which is incorporated by reference herein, and U.S. Provisional Patent Application No. 61/293,879, filed Jan. 11, 2010, STATIC AND DYNAMIC SEALS, ("STATIC AND DYNAMIC SEALS patent application"), which is incorporated by reference herein.

A pump (not illustrated) connected to port 5 of valve 102 may be used to push the sample out of needle 123 to the LC column (LC is connected at port 6) over a fluid path from port 5 to port 4, through connection 206a and to the needle 123, over connection 206b, and from port 1 to port 6.

Once the seal has been formed between surfaces of the needle tip and needle seal, an embodiment may perform needle washing while the sample is being injected into the system and analyzed as part of the chromatographic run. Needle washing may be performed by forcing a solvent or, more generally, a needle washing fluid, through the passageway 110. The passageway 110 included in the support structure, as illustrated in more detail herein, has the needle 123 inserted therein. While the needle tip and needle seal are engaged in forming the seal, needle washing fluid may be forced (such as using pump 122) along a path formed by 204a, valve 204b, 204c, 204d, input port 110a, through the passageway 110 surrounding the inserted needle 123, out port 110b, over connection 204e to valve 204f, over connections 204g and 204h to waste. The foregoing needle washing may commence at some point, such as during the chromatographic run or while the sample is being injected, after the seal has been formed. The needle washing may be performed for a predetermined amount of time. After the injection, and chromatographic run for the current sample are complete, the cycle defined and illustrated by FIGS. 3 and 4 may be repeated for a next sample volume.

It will be appreciated by those of ordinary skill in the art that needle washing may also be performed using port 110b as the input washing fluid port of passageway 110 and port 110a as the output washing fluid port of the passageway 110. With the foregoing variation, connections to the ports 110a and 110b may be modified so that port 110a is connected to waste and port 110b is connected to the washing fluid or solvent.

In existing systems without the techniques herein, needle washing may occur after completion of a current chromatographic run while the needle and needle seal are not engaged in forming the foregoing fluid tight seal. In such embodiments without use of the techniques herein, the amount of time it takes for a complete cycle of a sample volume increases. A complete cycle may be defined to include the amount of time needed to complete sample aspiration, a chromatographic run, and needle washing for a single sample volume. In embodiments without the benefit of techniques herein, the foregoing processing may occur consecutively with needle washing being performed last in a given cycle. In an embodiment in accordance with techniques herein, the needle washing may occur during, and prior to completion of, the chromatographic run.

The fluid used to wash the needle may be, for example, water, an aqueous solution, or more generally, any suitable solvent or fluid.

Figure 5:
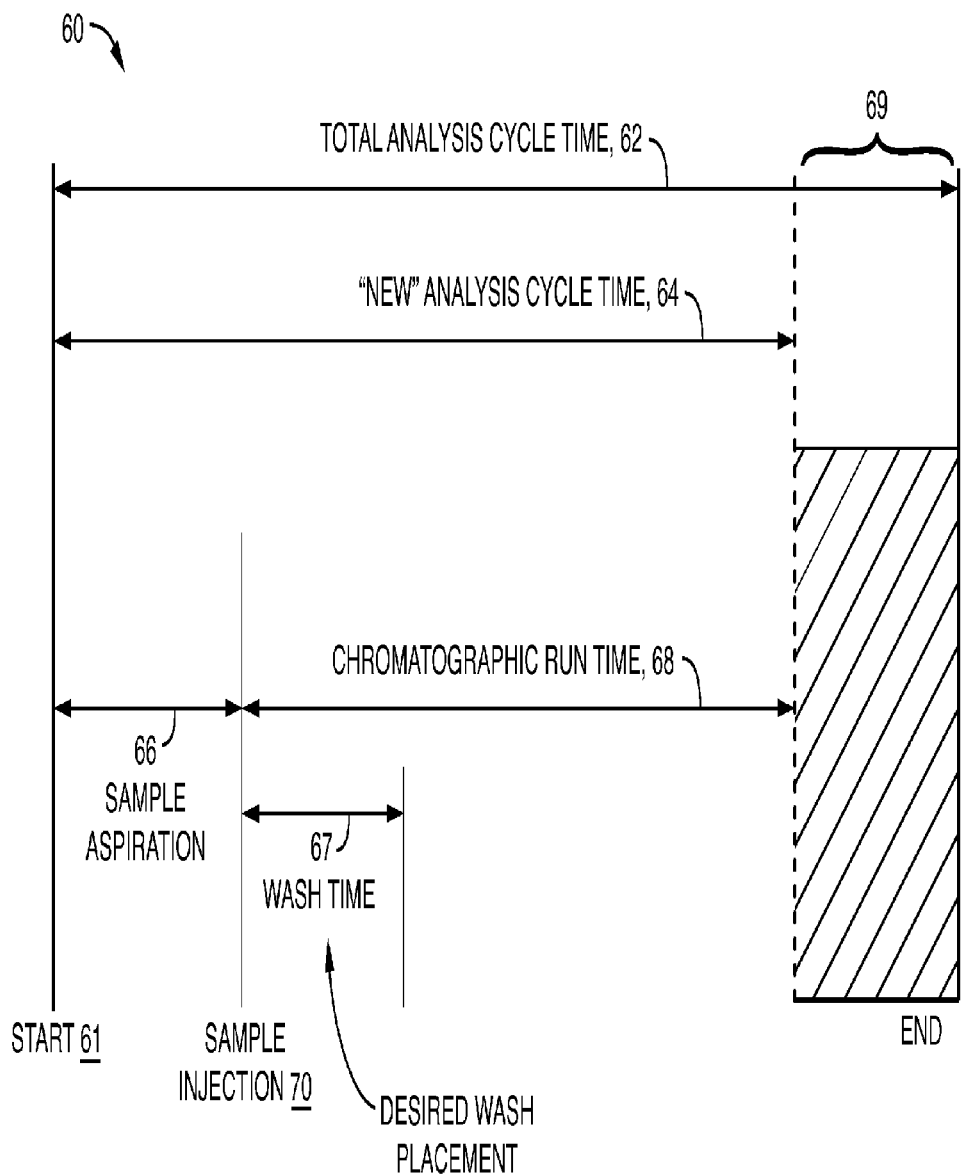
FIG. 5 is an example illustrating reduction of cycle time in an embodiment in accordance with techniques herein.

Referring to FIG. 5, shown is an example illustrating a cycle including needle washing that may be performed in an embodiment in accordance with techniques herein. The example 60 illustrates a total analysis cycle time, or cycle time 62 for an embodiment which performs sample aspiration, a chromatographic run, and needle washing consecutively. Element 66 represents the time for sample aspiration. Element 68 represents the time for the chromatographic run. Element 69 represents the time for needle washing in an embodiment without use of the techniques herein. Element 70 represents the point in time at which the seal is formed between surfaces of the needle tip and needle seal and injection of the sample volume in the needle into the system is commenced. At the start time 61, the injection valve may be in the load position and sample aspiration may be performed as illustrated and described in connection with FIG. 3. Subsequently, the needle is repositioned and inserted into the injection port with a sufficient force applied thereto to form a seal between surfaces of the needle tip and needle seal (included in the injection port assembly although not illustrated in FIGS. 3 and 4). Sample injection as represented by point 70 may occur by creating a fluid path which forces and carries the sample volume out of the needle to the LC column, or more generally a separation means, as described above in connection with FIG. 4.

The example 60 illustrates the total cycle time 62 in an embodiment which performs the foregoing tasks for a sample volume consecutively with no overlap as the sum of the time quantities represented by 66, 68 and 69. In contrast, an embodiment in accordance with techniques herein may perform needle washing while also performing the chromatographic run. Element 64 represents the total cycle time in such an embodiment in accordance with techniques herein. The example 60 illustrates that the total cycle time 64 in an embodiment in accordance with techniques herein which performs needle washing during the chromatographic run as the sum of the time quantities represented by 66 and 68. Element 67 represents the time at which the needle washing may be performed in an embodiment in accordance with techniques herein.

FIG. 5 shows one example of where the needle washing 67 may occur within a given single cycle in accordance with techniques herein. However, as will be appreciated by those skilled in the art, an embodiment in accordance with techniques herein may perform the needle washing more generally at anytime during the chromatographic run (e.g., anytime during the time interval represented by 68) or, more generally, at anytime during the cycle after the seal is formed between surfaces of the needle tip and needle seal and while such seal is formed.

Referring to FIG. 6, shown is an example of a needle seal, needle, and components of an embodiment of an injection port for use with direct injection in an LC system in accordance with techniques herein. The example 180 illustrates components of an injection port 181. The example includes a needle seal 184 that may be characterized as forming a dynamic seal during operation of a direct injection technique to introduce a sample into the LC system. In connection with performing direct injection, a sample may be aspirated into a needle, such as illustrated by 196. At a first point in time, the needle is then inserted into opening 182 with a sufficient downward force in the vertical direction into passageway 183 and into an opening 184a in the needle seal 184. The needle tip comes into contact with sidewalls within the opening 184a in the needle seal 184 to form a seal. Element 190 shows an enlarged view of a portion of the needle seal included in 181. As illustrated in further detail in 190, the opening 184a forms a throughhole through the needle seal. The inner sidewalls of 184a are tapered and narrowed to a point so that the needle tip, when inserted into 184a, comes into contact with the inner sidewalls of 184a as it narrows. It is at the foregoing points of contact between the needle tip and inner sidewalls that the seal is formed. At the first point in time during which the needle is inserted, there is no pressurization with respect to the needle seal. Once the needle is inserted into the needle seal 184 and an appropriate amount of force is present at the point of contact between the needle tip and needle seal sidewall surfaces within the opening 184a, fluid flow is turned on resulting in pressurization of the system. A seal is formed at the point of contact between the needle tip and inner sidewalls of 184a. The fluid flow through the needle is then stopped and the needle seal and system are still pressurized. At a second point in time, the needle is then pulled in the upward vertical direction along 183 out of the needle seal 184 causing depressurization. As described above, the needle is inserted at a first end, such as through 182, of the passageway 183 and the tip of the needle forms the seal when in contact with a surface of the needle seal at an opposing end of the passageway.

Element 187a denotes a needle support structure formed by 187 and having passageway 183. The support structure may also include the connections 111a and 111b in the illustrated embodiment. Passageway 183 may have a diameter, for example, within the range of 0.062+/−0.003 inches for use with the needle 196. The length of the needle support structure as measured from P1 to P2 may be 1.945+/−0.003 inches. It should be noted that the needle support structure may have other suitable dimensions to accommodate desired needle diameters and/or lengths that may be used in an embodiment.

In one embodiment, a needle 196 may be used which has a tapered tip so that the needle tip at a first point 196a has an outer diameter (OD) of 0.0.40+/−0.001 inches. The needle may be, for example, stainless steel. The needle tip may be tapered and narrowed from the first point 196a to the second point 196b where the outer surface of the needle tip comes into contact with the inner sidewalls of the needle seal. In one embodiment, the OD at the second point may be 0.013+/−0.001 inches. The needle tip may be tapered at a 13 degree angle as illustrated in 196. Element 190 illustrates some exemplary measurements in one embodiment of a needle seal 184 that may be used with the foregoing needle 196. The needle seal opening 184a may be narrowed as illustrated by tapering in accordance with the 20 degree angle to point 190a. From point 190a to point 190b the opening 184a may have a relatively uniform or constant diameter of 0.007 inches. The opening 184a may form a through hole through the needle seal 184 so that the needle enters at a first or top surface. Point 190b may be at a bottom surface of the needle seal opposing the foregoing top surface.

Also illustrated are ports 110a and 110b through which different solvents or other fluids may flow into/out of the injection port. Element 185 may be a port with tubing through which the sample flows out of once injected as described above. Element 185 may be connected, directly or indirectly, to an LC column. The amount of force applied and used in connection with the needle seal and inserted needle may be determined using any of a variety of techniques known in the art. For example, the needle seal embodiments described in the STATIC AND DYNAMIC SEALS patent application may be used in connection with direct injection with the techniques described in the NEEDLE SEAL FORCE SENSOR patent application. Some components illustrated in FIG. 6, such as the spring 188a and load cell 188b, may be optionally included in an embodiment of the injection port which uses a force sensor as described in the NEEDLE SEAL FORCE SENSOR patent application.

Element 183 represents a part of the support structure or needle support structure as described above such as represented (with reference to FIGS. 3 and 4) using element 110 of FIG. 3 and FIG. 4. Elements 110a, 110b, 111a, and 111b correspond to components as described above in connection with FIGS. 3 and 4. Connections 111a and 111b may be approximately perpendicular with respect to the passageway 183.

Element 183 may be formed within, or surrounded by, a material 187 such as stainless steel or one of a variety of different suitable PEEK (polyether-ether-ketone) materials known in the art. The material 187 facilitates holding the components of the injection port in an assembled arrangement as illustrated in FIG. 6. Additionally, the material 187, and passageway 183 formed therein, along with elements 110a, 110b, 111a and 111b may be characterized as forming the needle support structure in the example 180. Element 189a may be a component holding the seal. Element 189b may be a spacer. Element 189c may be a spring support or cup.

Figure 7:
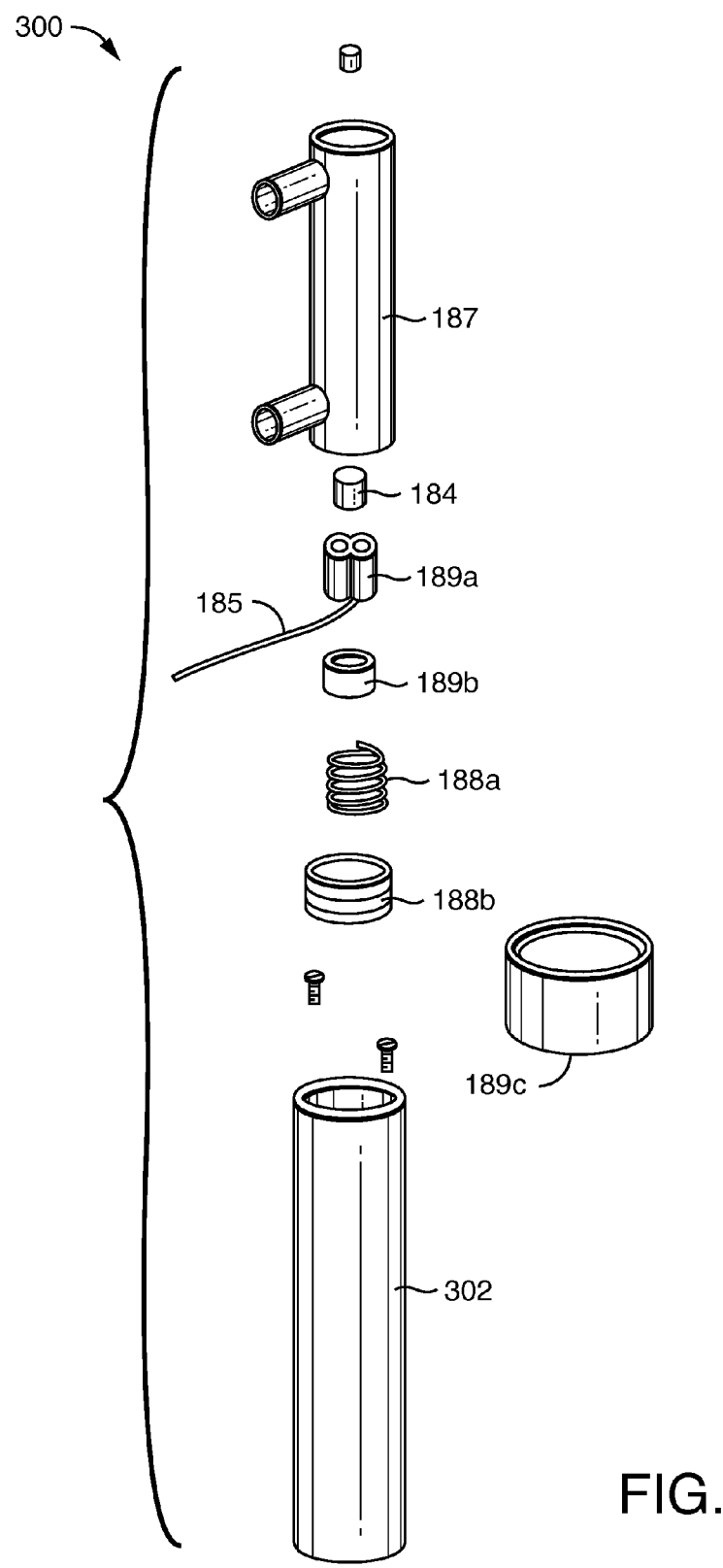

Referring to FIG. 7, shown is an example of a disassembled view of components of an embodiment of an injector port. The example 300 includes components of FIG. 6 within a housing 302. Component 189c may be interposed between the spring 188a and the load cell 188b. The components illustrated in FIGS. 6 and 7 may be made of any suitable material and manufactured using any suitable means and techniques known in the art. For example, as described above, the needle support structure material 187 as well as the connections 111a and 111b may be made of a PEEK material. The housing 302 may be made of aluminum. The spring 188a, tubing used in connection with 185, parts or components 189a and 189b, and spring support 189c may be made from stainless steel.

Due to the requirements that may be imposed on a needle and force applied thereto in a system performing direct injection, use of the techniques herein for additional needle support facilitate application of such required force to the needle without the needle buckling Additionally, incorporation of the needle support structure allows an embodiment to optionally include additional features in the needle support structure for performing needle washing. As described herein, such needle washing features allow an embodiment to perform needle washing at anytime during the cycle while the seal is formed between surfaces of the needle tip and needle seal (e.g., while the needle is engaged with the needle seal).

It should be noted that an embodiment may include the needle support structure features described herein alone, or in combination with, the additional features for needle washing. In an embodiment in which the support structure is desired without the features for needle washing, the passageway of the support structure into which the needle is inserted may have a smaller diameter than as described elsewhere herein since the passageway dimensions do not have to allow for usage of the wash fluid. In such an embodiment, the ports, connections, and other features which are included to exclusively facilitate needle washing in accordance with techniques herein may be omitted. For example, with reference to FIG. 6, another embodiment of a needle support structure may be denoted by dashed area 187a without features such as 111a and 111b.

As illustrated in connection with FIG. 6, needle seal surfaces are in contact with the passageway 183 and there is a substantially fluid tight connection therebetween. Similarly, there may be substantially fluid tight connections between 111b and 183, and between 111a and 183 included in the path of the washing fluid for needle washing. As will be appreciated by those skilled in the art, although not explicitly stated, connections between other components illustrated and described in FIG. 6 and others herein may also be characterized as fluid tight so as not to allow undesirable leakage of the sample, washing fluid, and the like.

Figure 8:
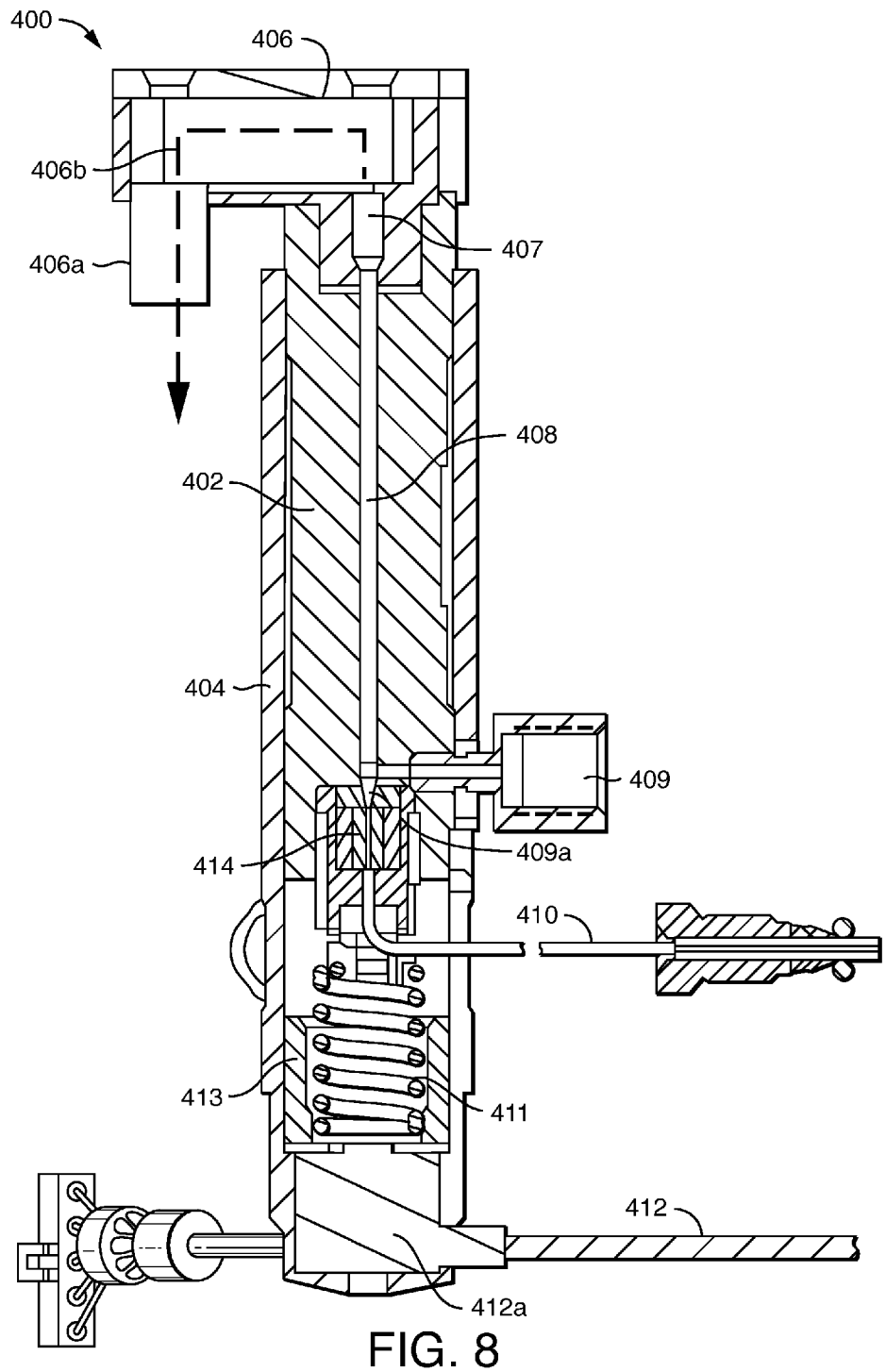
FIGS. 8, 9, and 10 are examples illustrating components that may be included an embodiment of an injection port in accordance with techniques herein.

Referring to FIG. 8, shown is an example of another embodiment of an injection port and its components in accordance with techniques herein. The example 400 includes components similar to those described in connection with the embodiment of FIGS. 6 and 7. As described in more detail below, a difference between the embodiments of example 400 and FIG. 6 relates to the features included and used in connection with needle washing.

The example 400 illustrates a lateral view of components of the injection port when assembled and includes housing 404, material 402 forming the needle support structure, passageway 408 of the support structure into which the needle is inserted, spring 411, spring support 413, tubing 410, load cell 412a, and needle seal 414. Additionally illustrated in this figure is a load cell cable 412. It should be noted that the embodiment of FIG. 6 also similarly includes a load cell cable 412 even though not illustrated. The embodiment of the example 400 includes a fitting having a port 409 and connection 409a to the passage 408. Additionally, the example 400 includes port 407 connected to passage 408. In the embodiment of 400, the washing fluid for needle washing in accordance with techniques herein flows through a path formed by 409, through connection 409a and passageway 408, and exits through port 407 which may be diverted to waste. Port 407 is connected to a wash overflow component 406 which may serve as an overflow area for washing fluid. Wash fluid collected in 406 may be diverted to waste via element 406a. In connection with performing needle washing using the embodiment of the example 400, the wash fluid flows into 409, over connection 409a, passageway 408, port 407, and then into component 406. As illustrated by 406b, wash fluid collected in 406 is then routed to waste via 406a.

Figure 9:
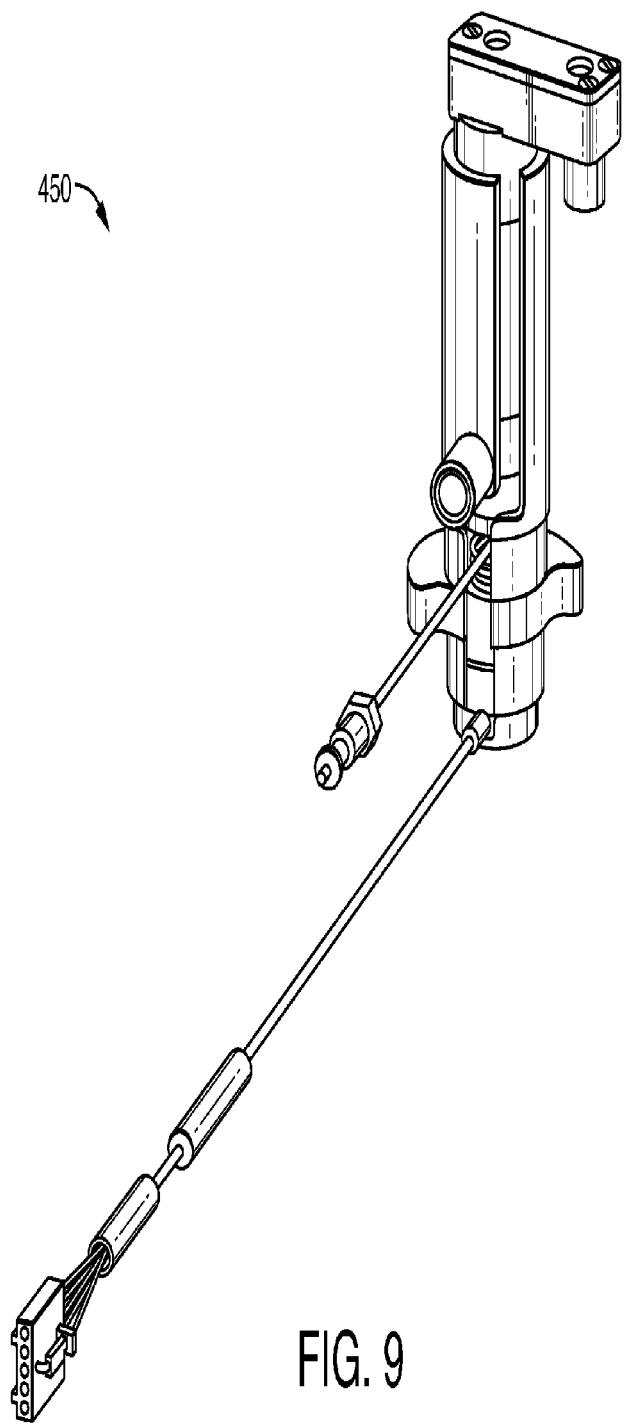

The example 400 illustrates a profile or lateral cross section view of the injection port embodiment. FIG. 9 shows another assembled view of the injection port embodiment of FIG. 8.

Figure 10:
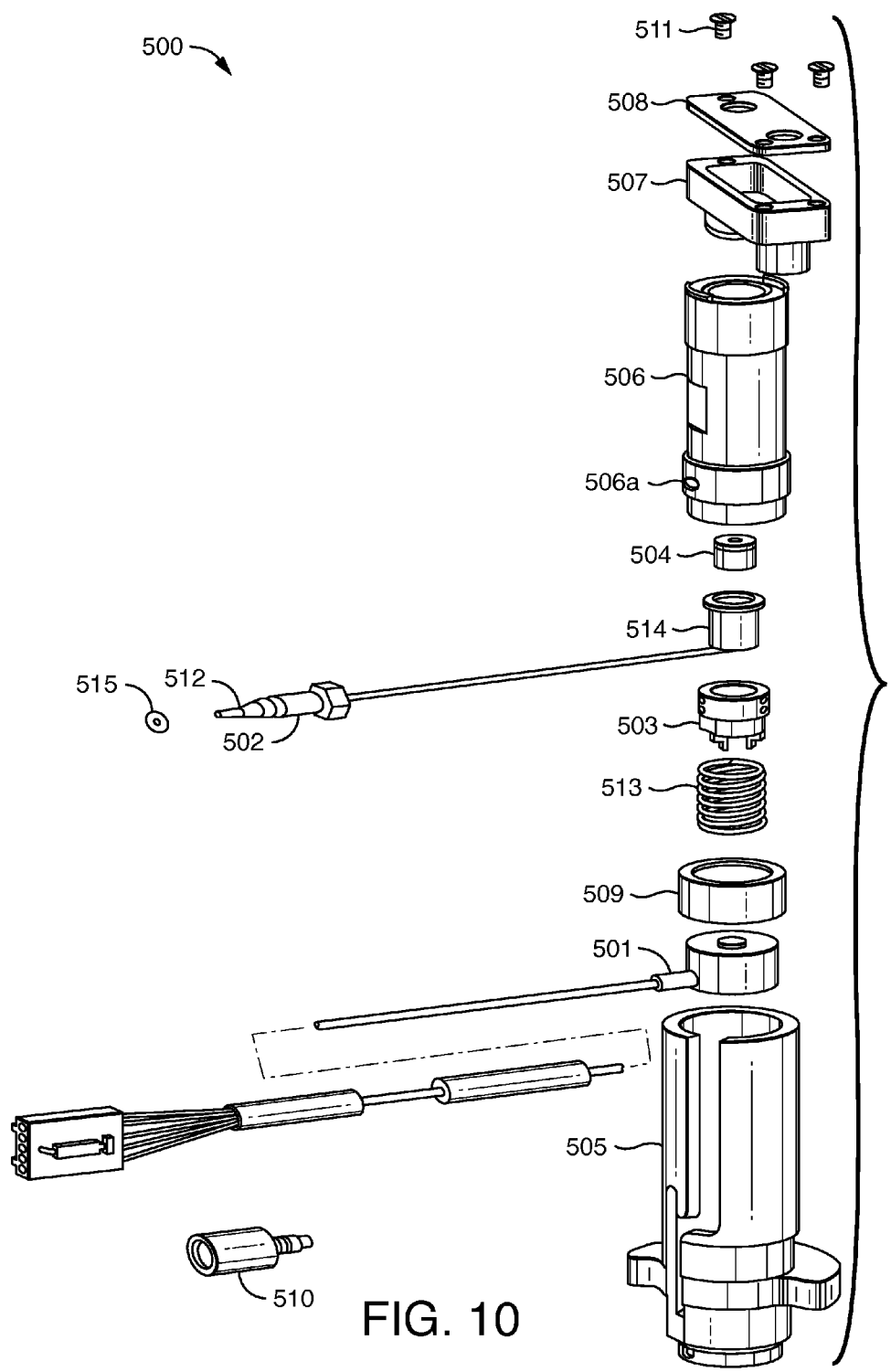

Referring to FIG. 10, shown is an example 500 illustrating a disassembled view of the components of the injector valve embodiment of FIGS. 8 and 9 in accordance with techniques herein. The example 500 includes a load cell and cable 501, a screw 502, port locking nut 503, needle seal 504, housing 505, needle support structure 506, overflow cup component 507, cap 508 for component 507, spring support or cup 509, fitting 510, screws 511, two-piece ferrule set 512, spring 513, an assembly 514 of a tube and support cup, and o-ring 515. It should be noted that element 510 may be installed in the fitting port 506a after the support structure 506 and related assembly is installed in the housing 505. With reference back to FIG. 8, element 510 may include the port 409 and may form the connection 409c to the passageway 408. Components of the example 500 may be made of materials similar to as described above in connection with the example 400. For example, 502, 503, 509, 511, 513 and 514 may be made of stainless steel; 505 may be made from aluminum; and 506, 507, 508 and 510 may be made from a PEEK material.

It should be noted that as with the embodiment of the injection port of FIG. 6, the needle washing fluid path described above may be reversed so that the washing solvent enters the passageway 408 through 407 and exits through 409.

It will be appreciated by those skilled in the art that any particulars related to materials, dimensions, and the like, as provided herein for example and illustration should not be construed as a limitation of the techniques herein.

While the invention has been disclosed in connection with preferred embodiments shown and described in detail, their modifications and improvements thereon will become readily apparent to those skilled in the art. Accordingly, the spirit and scope of the present invention should be limited only by the following claims.

What is claimed is:

1. An injection port comprising:
   a needle support structure configured to accommodate a needle containing a sample aspirated therein; and
   a needle seal having a throughhole into which one end of the needle is inserted in a vertical direction with a sufficient force applied thereto in the vertical direction, the needle seal having surfaces thereof in contact with surfaces of an end face of said one end of the needle, wherein said end face faces said vertical direction and a seal is formed where said surfaces of the needle seal contact the surfaces of the end face of the needle, wherein the needle support structure includes a passageway into which the needle is inserted when forming the seal and wherein the injection port is configured to pass washing fluid through the passageway while the needle is in the passageway.

2. The injection port of claim 1, wherein the injection port is included in a system that performs liquid chromatography.

3. The injection port of claim 1, wherein the material is one of a PEEK (polyether-ether-ketone) material or stainless steel.

4. The injection port of claim 1, wherein said needle support structure includes a first port connected to the passageway and a second port connected to the passageway.

5. The injection port of claim 4, wherein washing fluid enters the passageway through the first port and exits the passageway through the second port, said first port being connected to a solvent source used as said washing fluid and said second port is connected to waste.

6. The injection port of claim 5, wherein said first port is connected to the passageway through a first connection and said second port is connected to the passageway through a second connection.

7. The injection port of claim 6 wherein said first connection and said second connection are included in the needle support structure and approximately perpendicular with respect to the passageway.

8. The injection port of claim 4, wherein washing fluid enters the passageway through the first port connected approximately perpendicular to the passageway and exits through the second port connected to an opening at a top of the passageway into a wash overflow component which diverts to waste.

9. The injection port of claim 1, wherein the needle is inserted at a first end of said passageway and the end face of the needle forms the seal when in contact with the surfaces of the needle seal at an opposing end of the passageway.

10. The injection port of claim 1, wherein washing fluid passes through the passageway to wash the needle while a seal is formed between the surfaces of the needle seal in contact with the surfaces of the end face of the needle.

11. The injection port of claim 6, wherein the first port and the second port are both located at vertical positions above the needle seal.

12. The injection port of claim 11, wherein a third port is connected of the passageway and the third port connects to a liquid chromatography column, said third port being located at a vertical position below the first port, the second port and the needle seal.

13. A method of performing direct injection of a sample comprising:
   receiving a needle having the sample aspirated therein;
   inserting one end of the needle into a passageway of a needle support structure;
   applying a sufficient force to the needle downward in a vertical direction to form a seal between surfaces of an end face of said one end of the needle in contact with surfaces of a needle seal, said end face facing said vertical direction;
   transporting the sample from the needle over a fluid path to a liquid chromatography column for separation; and
   washing the needle with washing fluid that flows through the passageway while the needle is in the passageway.

14. The method of claim 13, wherein the needle support structure provides support for the needle to prevent buckling when pressure is applied thereto to form the seal.

15. The method of claim 13, wherein said washing the needle with washing fluid that flows through the passageway is performed while the seal informed.

16. The method of claim 15, wherein said washing is performed prior to completion of a chromatographic run of the sample.

17. The method of claim 13, wherein the needle is inserted at a first end of said passageway and the end face of the needle forms the seal when in contact with the surfaces of the needle seal at an opposing end of the passageway.

18. A method of performing direct injection of a sample comprising:
   receiving a needle having the sample aspirated therein;
   inserting one end of the needle into a passageway of a needle support structure;
   applying a sufficient force to the needle downward in a vertical direction to form a seal between surfaces of an end face of said one end of the needle in contact with surfaces of a needle seal, said end face facing said vertical direction;
   transporting the sample from the needle over a fluid path to a liquid chromatography column for separation; and
   washing the needle with washing fluid that flows through the passageway while the sample is being injected.

\* \* \* \* \*